(12) United States Patent
Harada et al.

(10) Patent No.: US 7,342,662 B2
(45) Date of Patent: Mar. 11, 2008

(54) SAMPLE ANALYZER

(75) Inventors: Kunio Harada, Hachioji (JP);
Sakuichiro Adachi, Hachioji (JP);
Hideo Enoki, Chiyoda (JP); Hironobu Yamakawa, Toride (JP); Tomonori Mimura, Tomobe (JP)

(73) Assignee: Hitachi High-Technologies Corporation, Tokyo (JP)

( * ) Notice: Subject to any disclaimer, the term of this patent is extended or adjusted under 35 U.S.C. 154(b) by 255 days.

(21) Appl. No.: 11/132,291

(22) Filed: May 19, 2005

(65) Prior Publication Data

US 2005/0259261 A1 Nov. 24, 2005

(30) Foreign Application Priority Data

May 21, 2004 (JP) ............................. 2004-151177

(51) Int. Cl.
*G01N 21/00* (2006.01)
(52) U.S. Cl. ..................................... 356/436
(58) Field of Classification Search ............... 356/436, 356/337
See application file for complete search history.

(56) References Cited

U.S. PATENT DOCUMENTS

| | | | | |
|---|---|---|---|---|
| 3,056,331 A | | 10/1962 | Sisson | |
| 4,573,796 A | * | 3/1986 | Martin et al. | 356/318 |
| 4,893,929 A | * | 1/1990 | Miyamoto | 356/336 |
| 4,999,513 A | * | 3/1991 | Ito et al. | 250/575 |
| 5,480,775 A | * | 1/1996 | Ito et al. | 435/7.2 |
| 2005/0200964 A1 | | 9/2005 | Kopp | |

FOREIGN PATENT DOCUMENTS

| | | |
|---|---|---|
| JP | 60-011143 | 1/1985 |
| JP | 08-122247 | 5/1996 |
| JP | 2001-159601 | 6/2001 |
| JP | 2002-340676 | 11/2002 |
| WO | 2004/034039 | 4/2004 |

\* cited by examiner

*Primary Examiner*—Tarifur Chowdhury
*Assistant Examiner*—Isiaka O Akanbi
(74) *Attorney, Agent, or Firm*—Antonelli, Terry, Stout & Kraus, LLP.

(57) ABSTRACT

The adverse effect on measurement accuracy brought about by the transmission of light beams through portions of a liquid sample with different concentrations, i.e., a concentration distribution in the vertical direction of a container, is prevented by using semiconductor light sources of two different types with different wavelengths. The semiconductor light sources (2, 4) of two different types are housed in the same package (5) such that a detector (9) can capture the light beams emitted by the light sources after their optical axes have intersected with one another. The multiple light beams can be thus caused to pass through portions with substantially the same concentration and therefore can be detected without being influenced by the difference in concentration of the sample in the container.

12 Claims, 8 Drawing Sheets

FIG.3
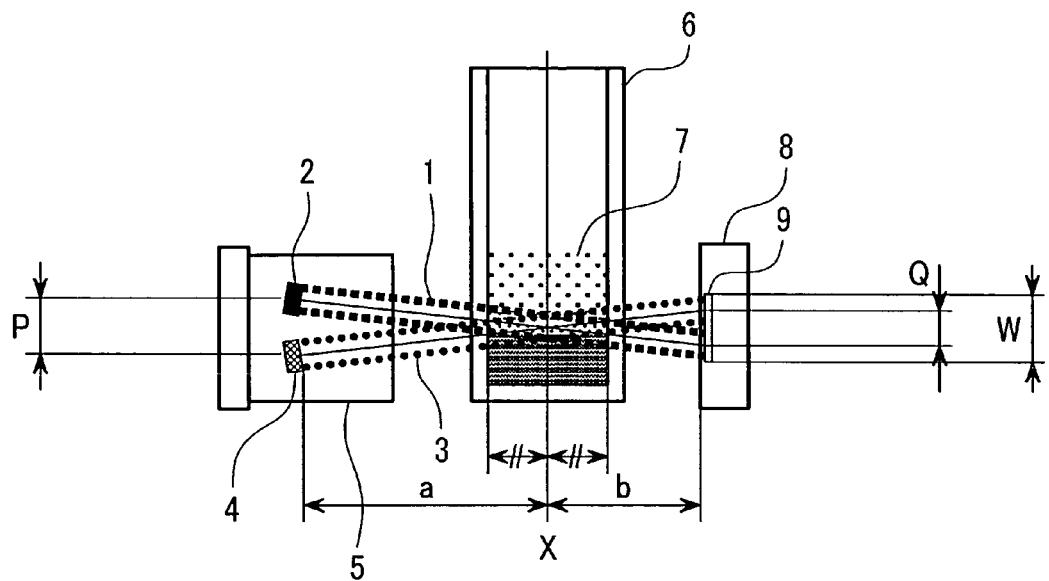
FIG.4A      FIG.4B
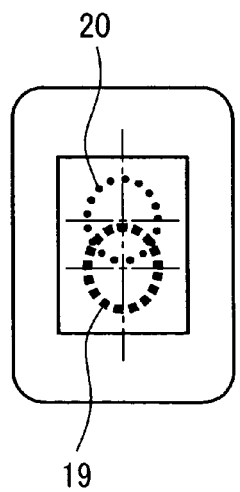   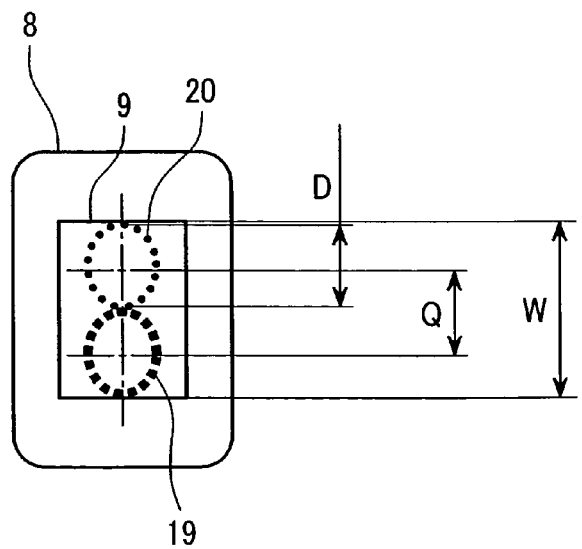

·········· : IRRADIATE LIGHT (WAVELENGTH : λ1)

·········· : IRRADIATE LIGHT (WAVELENGTH : λ2)

■■■■■■■ : IRRADIATE LIGHT (WAVELENGTH : λ1)

•••••••• : IRRADIATE LIGHT (WAVELENGTH : λ2)

— — — : REFLECTED LIGHT

SAMPLE ANALYZER

CLAIM OF PRIORITY

The present application claims priority from Japanese application JP 2004-151177 filed on May 21, 2004, the content of which is hereby incorporated by reference into this application.

BACKGROUND OF THE INVENTION

1. Field of Invention

The invention relates to an analyzer for detecting the amounts of components contained in a sample.

2. Related Art

As an analyzer for detecting the amounts of components contained in a sample, a spectroscopic analyzer is widely employed whereby a sample solution is irradiated with white light such as emitted by a halogen lamp. The light beam that has passed through the sample solution is split by a diffraction grating to extract necessary wavelength components, and the amounts of target components are measured by determining their absorbance. The light emitted by e.g., a halogen lamp, however, cannot be narrowed in order to obtain an intensity of light commensurate with a sample solution that has been thinned by reducing its volume. Thus, there is a limit to the extent to which the amount of a sample solution can be reduced.

In response, it has been proposed to use a semiconductor light source capable of producing a narrowed light beam with sufficient intensity for a sample solution that has been thinned by reducing its volume. For example, JP Patent Publication (Kokai) No. 8-122247 A (1996) discloses an analyzer comprising a laser or LED element as the light source, whereby a sample container is irradiated with light beams of a plurality of wavelengths, and absorbance is measured in a plurality of wavelength regions. In another example, JP Patent Publication (Kokai) No. 2001-159601 A discloses that a plurality of semiconductor light sources, such as LEDs or laser diodes, are used, and a sample container is irradiated with light beams such that the optical axes of a plurality of light beams are aligned into one axis using an optical mechanism including a combination of prisms and half mirrors. Further, JP Patent Publication (Kokai) No. 2002-340676 A discloses that a sample container is irradiated with light emitted by a plurality of LEDs with the emission wavelength $\lambda n$ modulated with different frequencies $fn$, wherein transmitted light is A/D converted and then integrated for frequency analysis.

Patent Publication 1: JP Patent Publication (Kokai) No. 8-122247 A (1996)

Patent Publication 2: JP Patent Publication (Kokai) No. 2002-340676 A

Patent Publication 3: JP Patent Publication (Kokai) No. 2001-159601 A

SUMMARY OF THE INVENTION

Normally, a liquid sample exhibits different concentrations in the vertical direction due to the difference in specific gravity. Therefore, when irradiating the sample with light beams in the horizontal direction, measurement accuracy is adversely affected unless the light beams are caused to pass through a portion of the sample with the same concentration. In the examples of JP Patent Publication (Kokai) No. 8-122247 A (1996) or JP Patent Publication (Kokai) No. 2002-340676 A, a concentration distribution is produced in the vertical direction of the container if the measured article is a liquid. As a result, the individual light beams pass through portions with different concentrations, thereby adversely affecting the measurement accuracy.

Meanwhile, in the example of JP Patent Publication (Kokai) No. 2001-159601 A, the optical axes of a plurality of light beams are aligned into one axis by an optical device made up of prisms and half mirrors, for example. Thus, the multiple light beams are caused to pass through the same concentration, such that there is no adverse effect on measurement accuracy due to the difference in concentrations. However, the amount of light is reduced by the individual beams with different wavelengths passing through the prisms or half mirrors, so that a sufficient intensity cannot be obtained for the light that is passed through the sample solution, thereby adversely affecting the measurement sensitivity and measurement accuracy. In addition, the optical device consisting of a combination of prisms and half mirrors is expensive, and its optical axis adjustment is difficult to be made, leading to an increase in the cost of the system.

The aforementioned problems of the related art are solved by the following means in accordance with the invention:

(1) An analyzer is provided that comprises semiconductor light sources of at least two types with different output wavelengths, a sample container, and a detector. The semiconductor light sources are disposed such that the axes of the light beams emitted by the light sources can intersect with one another at a substantially ½ position of the length of a sample solution in the direction of transmission of light.

In this way, the optical axes of the light beams can be caused to overlap upon one another in the sample before the light beams are detected. Thus, the multiple light beams are caused to pass through portions with substantially the same concentration, so that the influence upon detection of the difference in concentration of the sample in the sample container can be reduced.

(2) Alternatively, the semiconductor light sources of at least two types and a photoreceiving element are housed in the same package and are arranged such that the light beams emitted by the light sources are incident on the sample container via a transparent plane that is disposed opposite to and in parallel with the sample container. The light beams then pass through the sample and intersect with one another substantially at a reflecting plane of the container before they are reflected thereby. The reflected beams of light then pass through the sample again and are eventually captured by the detector.

In this configuration too, the multiple beams of light can be caused to pass through portions of substantially the same concentration, so that the beams of light can be detected without being much influenced by the difference in concentration of the sample in the container.

(3) In another aspect, an analyzer comprises semiconductor light sources of at least two types with different output wavelengths, a sample container, and a detector. The optical axes of the light beams from the light sources are caused to intersect with one another between the light source and the detector, with an aperture provided at the point of intersection. In this way, unwanted stray light can be eliminated without affecting the light from the light sources, thereby improving the detection accuracy.

In accordance with the invention, the optical axes can be aligned without employing expensive equipment consisting of prisms and half mirrors, so that the multiple beams of light can be caused to pass through portions of the sample with substantially the same concentration and can therefore be detected without being influenced much by the difference in concentration of the sample in the container.

BRIEF DESCRIPTION OF THE DRAWINGS

FIG. 3 shows two semiconductor light sources, a sample solution in a container, and a detector in accordance with the invention, together with the thickness of the optical axes or the like.

FIGS. 4A and 4B show the light beam 1 with the wavelength λ1 and the light beam 3 with the wavelength λ2 as shone on the detector.

DESCRIPTION OF THE PREFERRED EMBODIMENTS

Best modes of implementing the invention will be hereafter described in detail.

Embodiment 1

In this embodiment, the output optical axes of the emitted beams are caused to intersect with one another at a position corresponding to substantially ½ of the length of light beams in the sample solution in the direction of transmission of light therethrough.

Figure 1:
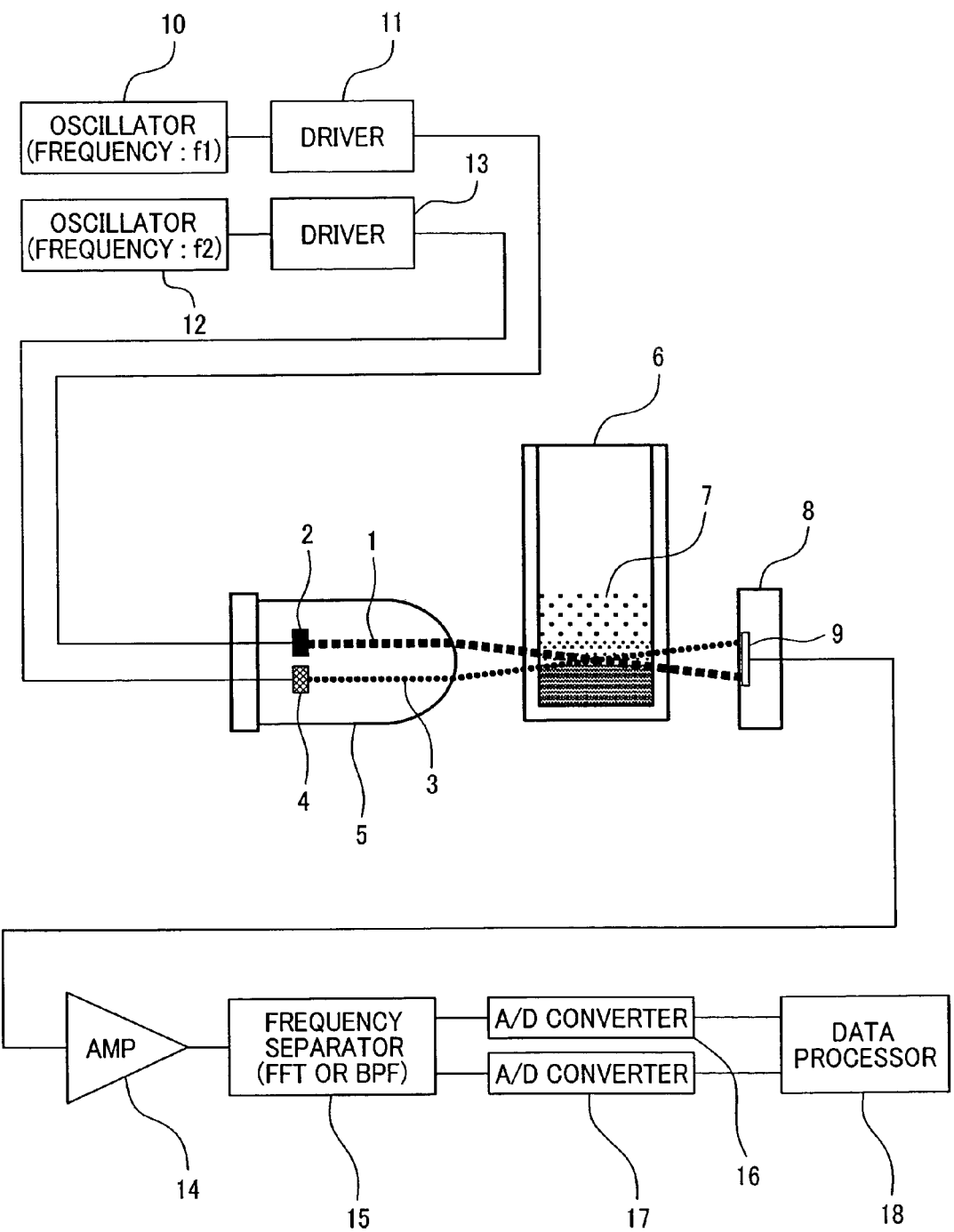
FIG. 1 schematically shows the structure of an analyzer according to the invention.

FIG. 1 is a schematic diagram of the analyzer. A semiconductor light source 2 that emits light beam 1 with the wavelength λ1 and a semiconductor light source 4 that emits light beam 3 with the wavelength λ2 are contained in a package 5 made of a transparent resin or the like. The light beam 1 with the wavelength λ1 and the light beam 3 with the wavelength λ2 emitted by the semiconductor light sources 2 and 4, respectively, in the package 5 are passed through a container 6 made of, e.g., a transparent resin or glass, and a sample solution 7 in the container. The light beams 1 and 3 are then shone on a detector 9 contained in a detector package 8 and are then detected by the detector. The position of the semiconductor light source 2 and that of the semiconductor light source 4 are adjusted within the package 5 such that the light beam 1 with the wavelength λ1 and the light beam 3 with the wavelength λ2 emerging from the package 5 intersect with one another at a position in the sample solution 7 corresponding to substantially ½ of the length of the light beams in the sample solution in the direction of transmission, as shown in FIG. 1, before they impinge on the detector 9. By "substantially ½" herein is meant that the point of intersection may not be exactly ½ and could be somewhat displaced from the precise center.

Normally, a liquid sample exhibits different concentrations in the vertical direction (i.e., the direction of gravity) over time due to differences in specific gravity. Specifically, portions of the sample solution with higher concentrations move to the bottom, while portions with lower concentrations move to the top, due to the difference in specific gravity of the components of the sample. Accordingly, when irradiating the sample with light in the horizontal direction for analysis, the measurement accuracy would be adversely affected unless the two beams of light pass through portions of the sample solution with the same concentration. This problem is prevented by causing the light beams to intersect with one another at a point in the sample solution corresponding to substantially ½ of the length of light in the direction of transmission, before the detector is irradiated with the light beams, as mentioned above. In this way, the influence of the difference in the transmitted paths of the two beams of light due to different concentrations can be reduced, enabling measurement with smaller variations.

Figure 2:
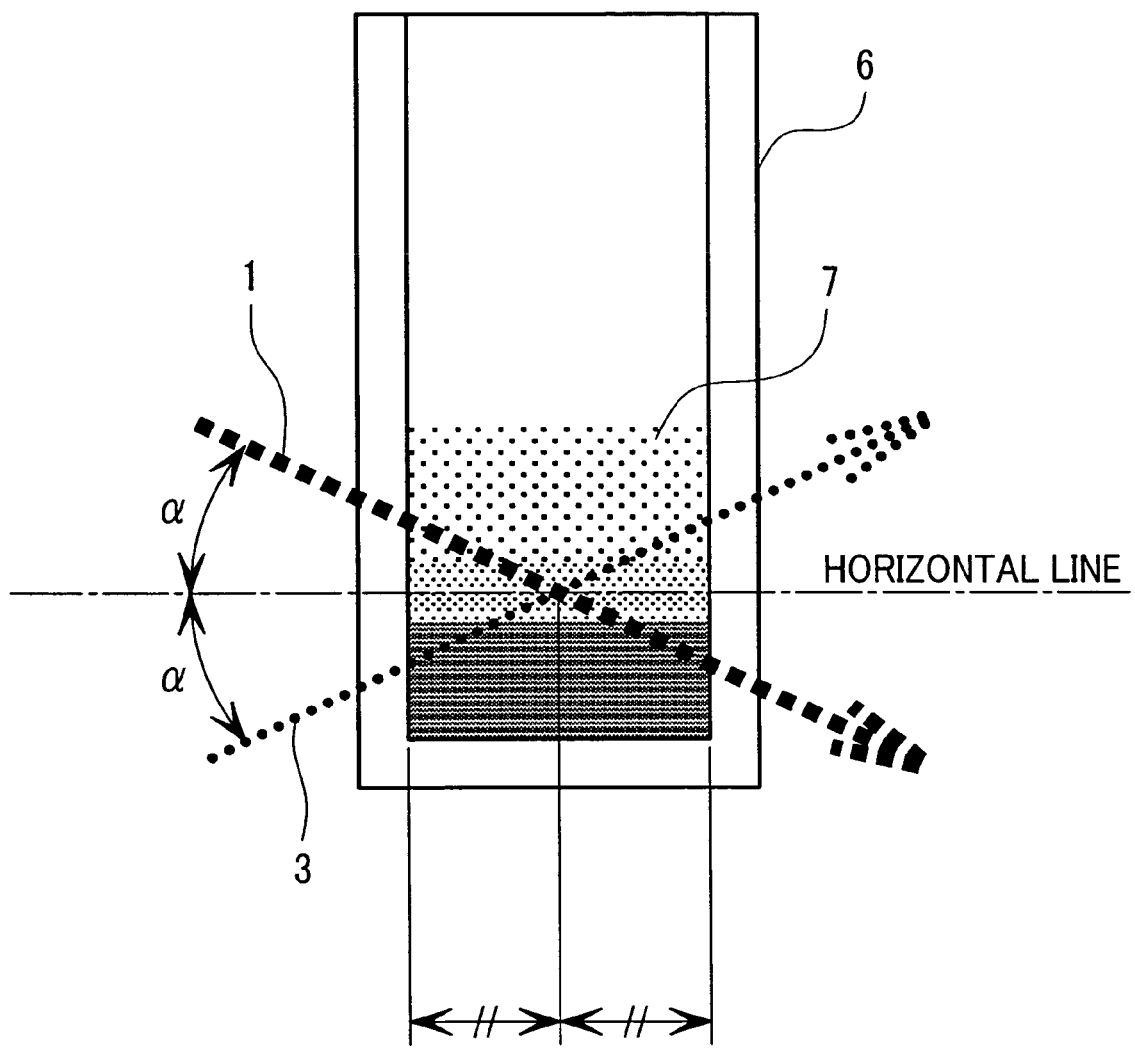
FIG. 2 shows a container 6 and a sample solution 7 of the analyzer of FIG. 1 in enlargement, with an angle α of a beam of light 1 with the wavelength λ1 and a beam of light 3 with the wavelength λ2 transmitted through the container with respect to the horizontal axis being exaggerated.

FIG. 2 shows a partially enlarged view of FIG. 1, showing the portions of the container 6 and the sample solution 7 in enlargement and also showing the angle α of the transmitted light beams 1 and 2 with the wavelengths λ1 and λ2 with respect to the horizontal axis, in an exaggerated manner. With reference to the example of FIG. 2, the light beam 1 with the wavelength λ1 emitted by the semiconductor light source 2 is incident on the sample solution from upper left to lower right. Namely, it propagates from a portion of the sample solution with a smaller concentration and is then transmitted in the direction of portions with higher concentrations, forming only a slight angle α with respect to the horizontal axis. On the other hand, the light beam 3 with the wavelength λ2 emitted by the semiconductor light source 4 is incident on the sample solution from lower left to upper right, namely, from a portion of the sample solution with higher concentrations, the light beam then being transmitted in the direction of lower concentrations, also with a slight angle α with respect to the horizontal axis. The concentrations of the sample solution 7 are horizontally symmetric (symmetric with respect to the vertical axis). Therefore, the light beam 1 with the wavelength λ1 and the light beam 3 with the wavelength λ2 pass through portions with the same concentrations in different directions. In the above example, the angle α is formed by the light beams 1 and 2 with the wavelengths λ1 and λ2 above and below the horizontal axis. However, in a case where the beams 1 and 3 with the wavelengths λ1 and λ2 each form an angle in opposite sides of the sheet of the drawing with respect to the horizontal axis, namely, when the light beams 1 and 3 with the wavelengths λ1 and λ2 are substantially in the same horizontal plane, the light beams 1 and 3 pass through portions with the same concentration and they are not influenced by the concentrations even though they have different optical transmission paths. This is true whether or not they intersect with one another at the substantially ½ length position in the sample solution 7 in the direction of transmission. However, in a biochemical automatic analyzer that detects the amounts of components in a sample by measuring the amount of light reduced by absorption or scattering, normally a container is horizontally moved while being irradiated with light. Thus, if the light beams 1 and 3 with the wavelengths λ1 and λ2 were to spread together in the horizontal plane, the time in which the two beams of light can be measured without their relevant portions being blocked would decrease, thereby adversely affecting the measurement accuracy.

The semiconductor light sources 2 and 4 are housed in the package 5 such that the light beams 1 and 3 with the wavelengths λ1 and λ2, after passing through the sample solution 5 under the aforementioned conditions, are shone on the detector 9 without loss. The simple structure, which does not employ expensive optical equipment consisting of prisms and half mirrors for causing the optical axes of light beams of two different wavelengths to be aligned, can produce the same effects as obtained in the case of using such expensive optical equipment. Thus, an optical system capable of detecting minute amounts of sample in a solution with high sensitivity and accuracy can be provided.

Referring to FIG. 1, the analyzer includes an electric signal processing system installed around the above-described optical components, as shown in a block diagram. A signal with the frequency f1 oscillated by an oscillator circuit 10 is amplified by a drive circuit 11 and then fed to the semiconductor light source 2, so that the semiconductor light source 2 can emit the light beam 1 with the wavelength λ1 and the modulation frequency of f1. Similarly, a signal with the frequency f2 is oscillated by an oscillator circuit 12, amplified by a drive circuit 13, and then fed to the semiconductor light source 4, so that the semiconductor light source 4 can emit the light beam 3 with the wavelength λ2 and the modulation frequency f2.

In this case, the voltage and current required by the semiconductor light sources are usually very small as compared with the ratings of the components of the oscillator circuits 10 and 12. Therefore, the oscillator circuit 10 may incorporate the function of the drive circuit 11 and the oscillator circuit 12 that of the drive circuit 13.

The light beam 1 with the wavelength λ1 and modulation frequency f1 emitted by the semiconductor light source 2 and the light beam 3 with the wavelength λ2 and modulation frequency of f2 emitted by the semiconductor light source 4 pass through the sample solution 7 along the aforementioned paths and are eventually detected by the detector 9.

The detector 9 converts the light beams 1 and 3 with the wavelengths λ1 and λ2 and modulation frequencies of f1 and f2, which are attenuated and composed by the sample solution 7 or the like, into an electric signal. The electric signal outputted from the detector 9, which consists of the frequencies f1 and f2, is amplified by an amplifier 14 and then separated into the individual frequency components f1 and f2 by a frequency separation circuit 15 comprised of an FFT or BPF, for example.

The signals with the frequencies f1 and f2 separated by the frequency separation circuit 15, which are analog signals, are converted into digital signals, the former by an A/D converter 16 and the latter by an A/D converter 17. The digital signals are then sent to a data processing unit 18.

Of the signals separated by the frequency separation circuit 15, the signal with the frequency f1 contains the information regarding the wavelength λ1, enabling comparison as to how much the light beam 1 with the wavelength λ1 has been attenuated by the sample solution 7 or the like. Similarly, the signal with the frequency f2 separated by the frequency separation circuit 15 contains information about the wavelength λ2, enabling comparison as to how much the light beam 3 with the wavelength λ2 has been attenuated by the sample solution 7 or the like. The reference for the comparison is the measurement data obtained in the case where the container 6 does not contain the sample solution 7, or the measurement data obtained with a reference reagent, such as purified water. By performing these processes using the data processing unit 18 and comparing the amount of attenuation of the light beam 1 with the wavelength λ1 and that of the light beam 3 with the wavelength λ2, the amount of a target component contained in the sample solution 7 can be detected.

By thus employing semiconductor light sources with different frequencies and the principle of a lock-in amplifier, an analyzer can be constructed which is capable of acquiring required frequency components without a diffraction grating and determining the amounts of target components by calculating their absorbance.

Regarding the optical paths within the sample container, portions that could have an adverse effect on detection are preferably avoided, such as the surface of the sample where there is surface tension, or the bottom of the container, for example.

Examples of sample include those containing components with different specific gravities, such as blood serum and blood plasma.

Embodiment 2

In the present embodiment, it is described how the distance between the semiconductor light sources 2 and 4 is determined depending on the positional relationship among the semiconductor light sources, the sample solution, and the detector. In embodiment 1, the light beams 1 and 3 with the wavelengths λ1 and λ2 emitted from the two different semiconductor light sources have been described with reference to the package 5 made of a transparent resin mold member or the like with accompanying refraction. In the present embodiment, reference is made to FIGS. 3 and 4. FIG. 3 shows two different semiconductor light sources, a sample solution in a container, and a detector, together with the indications of the thickness of optical axes or the like. FIG. 4 shows light beams 1 and 3 with the wavelengths λ1 and λ2 incident on the detector. The electric signal processing system shown in FIG. 1 will be omitted in the descriptions referring to FIG. 3 and subsequent figures.

The semiconductor light sources 2 and 4 are accommodated in the package 5 and adjusted such that the light beams 1 and 3 with the wavelengths λ1 and λ2 emitted thereby can intersect with one another at the position in the sample solution 7 that is substantially ½ of the length of the light beams in their directions of transmission, before they are incident on the detector 9. In this way, the influence of concentration arising from the difference in optical paths along which the two beams of light travel can be reduced, such that the measurement accuracy is less affected, as mentioned above. This effect can be expressed by a mathematical expression as follows.

Namely, the distance P between the semiconductor light sources 2 and 4 must be such that the relationship $P < a/b(W-D)$ is satisfied, where a is the distance between the semiconductor light sources 2 and 4 and X, which is the substantially ½ position of the length of the light beams in the sample in the direction of transmission in the horizontal direction with reference to FIGS. 3 and 4; b is the distance between X and the detector 9; W is the width of the photo-receiving plane of the detector 9; D is the maximum diameter on the photo-receiving plane of the light beams 1 and 3 with the wavelengths λ1 and λ2 emitted by the semiconductor light sources 2 and 4, respectively; and Q is the distance between the centers of the light beams 1 and 3 with the wavelengths λ1 and λ2 as projected on the detector 9.

In this case, the light beams 1 and 3 with the wavelengths λ1 and λ2 are incident on the photo-receiving plane of the detector 9 not perpendicularly but with a slight angle with respect to the normal to the plane. As a result, the light beams 1 and 3 with their wavelengths λ1 or λ2 produce a projection 19 and a projection 20, respectively, as shown in FIG. 4, which are slightly larger than the diameter of the cross-section of each of the light beams 1 and 3 taken in the direction perpendicular to their respective optical axes. Thus, in a case where the cross-section of the light beams 1 and 3 taken perpendicularly to their optical axes is circle, the projections 19 and 20 would be elliptical, with the diameter D indicating the maximum length of the projection. The effect of the projections 19 and 20 of the light beams 1 and 3, respectively, are the same whether they are spaced apart from one another, as shown in FIG. 4(*b*), or overlapped, as shown in FIG. 4(*a*), on the photo-receiving plane of the detector 9.

Figure 5:
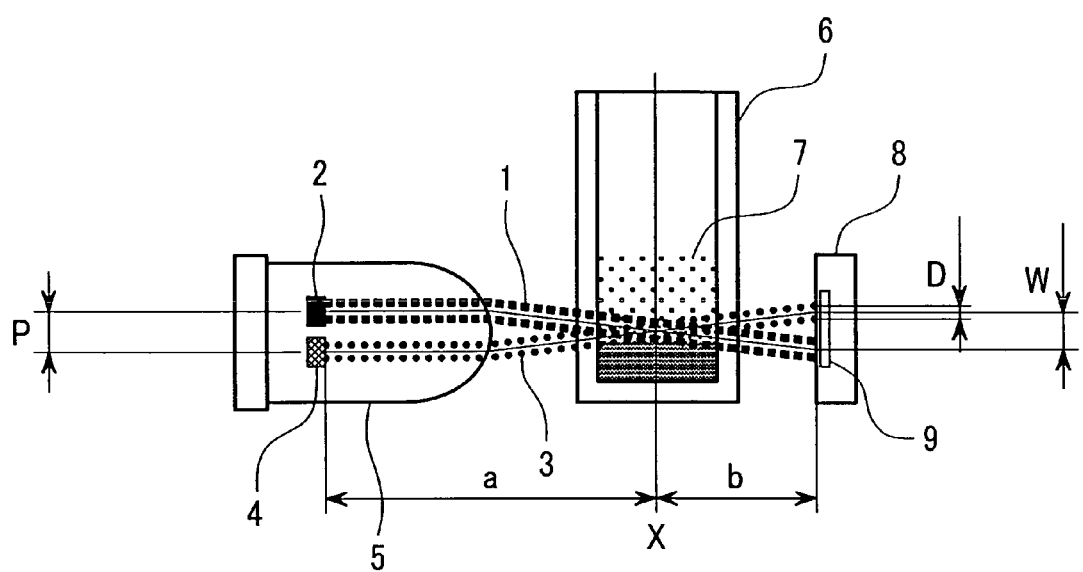
FIG. 5 shows the concept of Embodiment 2 as implemented in the example of Embodiment 1.

FIG. 5 shows the above-described concept implemented in Embodiment 1.

Embodiment 3

Embodiments 1 and 2 related to examples in which the first and second light beams are hardly diffused because of the use of semiconductor lasers, for example, in the light sources. However, when the light sources are light-emitting diodes, for example, the light emitted by the device would be diffused, such that the light beams would have to be narrowed in the event that the volume of the sample solution is very small.

Figure 6:
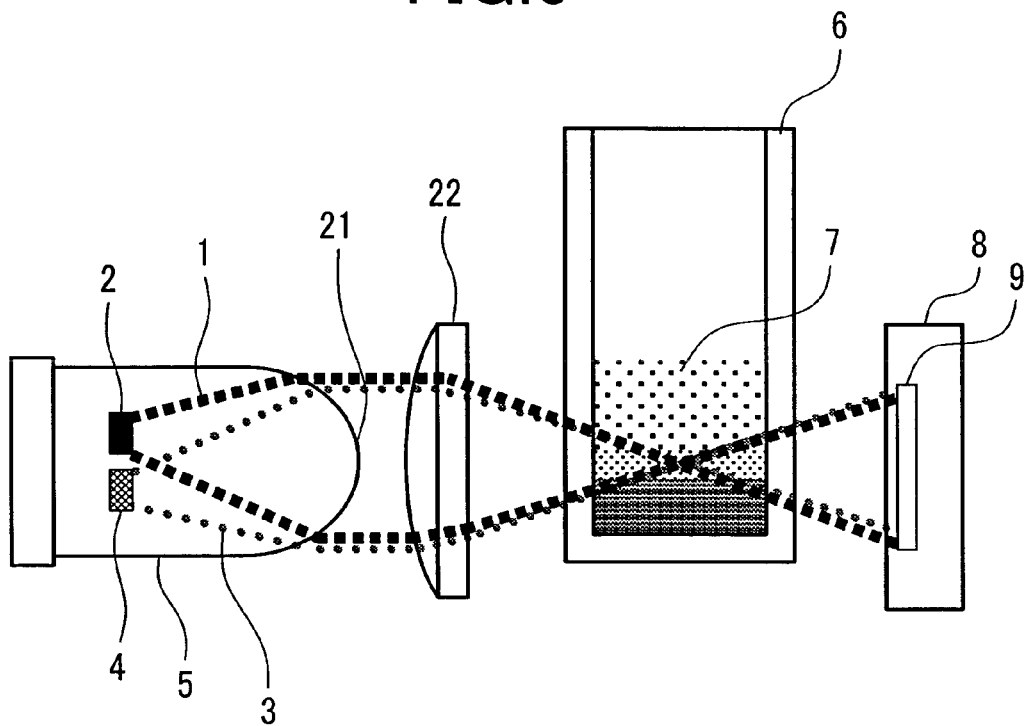
FIG. 6 shows an example where the light sources are formed by light-emitting diodes in accordance with the invention.

FIG. 6 shows an embodiment involving the use of, e.g., light-emitting diodes in the light sources. The semiconductor light sources 2 and 4 emitting light beams 1 and 3 with the wavelengths λ1 and λ2, respectively, are housed in a package 5 made of a transparent resin, for example. A tip portion 21 of the package 5 via which the light beams emerge is formed in the shape of a convex lens so that the outgoing light beams from the internal light sources can be formed into substantially parallel light beams. Thus, the light beams 1 and 3 with the wavelengths λ1 and λ2 emitted from the internal semiconductor light sources 2 and 4 in the package 5, respectively, are formed into substantially parallel beams with a large distance therebetween when they emerge from the package 5.

The thus widely formed parallel beams of light beams 1 and 3 with the wavelengths λ1 and λ2 are then focused by a lens 22 at the substantially ½ position in the sample solution 7 of the length of the beams in the direction of transmission. The beams then pass through the sample solution while again being spread, and they are eventually shone on the detector 9. In this embodiment, too, the beams 1 and 3 with the wavelengths λ1 and λ2 are not influenced by the concentrations of the sample due to the difference in their optical paths, as in Embodiments 1 and 2.

Embodiment 4

In Embodiments 1 to 3, the amounts of components in the sample are determined by detecting an optical signal from a detector on which two beams of light with different wavelengths that have passed through the sample solution in a container are incident. In embodiment 4, the analyzer is adapted such that, after the two beams of light with different wavelengths pass through a sample solution in a container, they are reflected by a wall surface of the container on the opposite side to the incident plane. The beams again pass through the sample solution and then detected by a detector housed in a package together with the semiconductor light source with the two different wavelengths.

Figure 7:
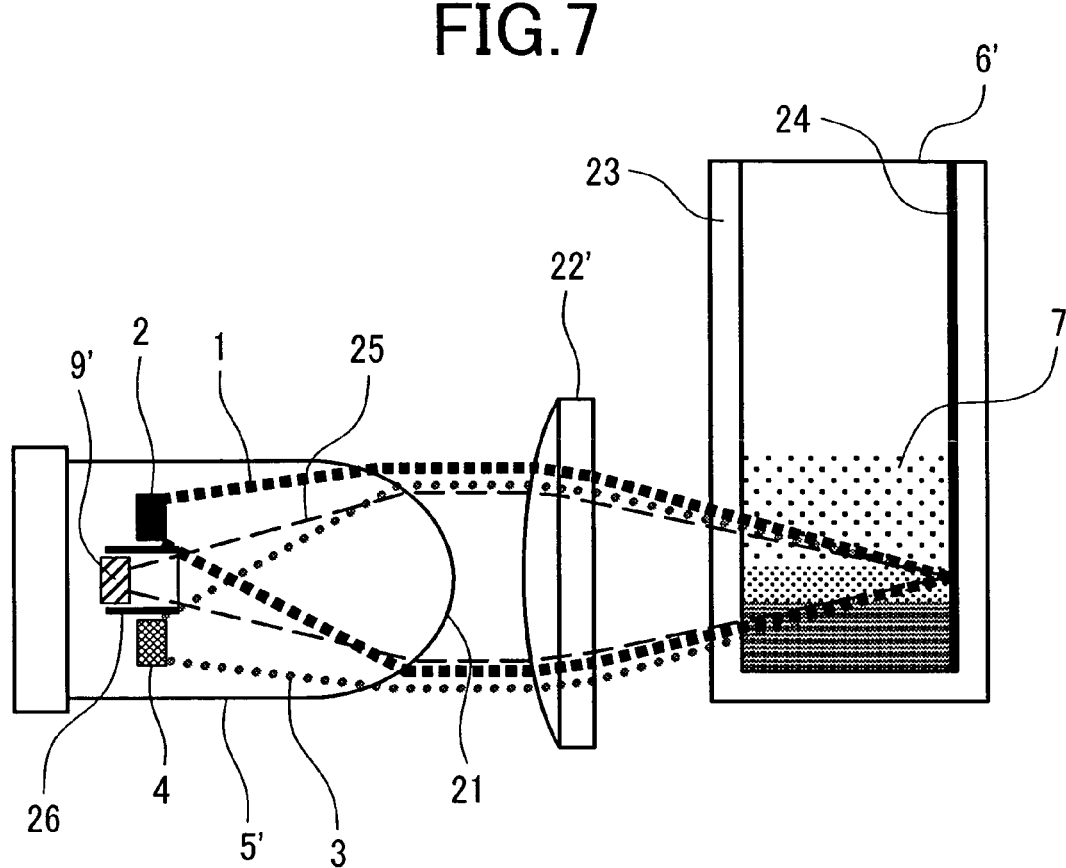
FIG. 7 shows an embodiment of the invention in which a detector is housed in the same package together with the two semiconductor light sources with different wavelengths.

FIG. 7 shows the present embodiment in which the detector is housed in the same package containing the semiconductor light sources with the two different wavelengths. The embodiment involves an example where the light beams emitted by the light sources, such as light-emitting diodes, are diffused, as in Embodiment 3. However, semiconductor lasers, the light emitted from which is not diffused, may be similarly employed as the light sources.

The semiconductor light source 2 emitting light beam 1 with the wavelength λ1 and the semiconductor light source 4 emitting light beam 3 with the wavelength λ2 are both housed in a package 5' made of a transparent resin, for example. In the present embodiment, furthermore, a detector 9', which corresponds to the detector 9 that has been disposed on the opposite side to the light sources with respect to the sample solution 7 in Embodiments 1 to 3, is housed in the same package 5' as for the semiconductor light sources 2 and 4. Further, a container 6' in which the sample solution 7 is contained is constructed with a wall surface 24. The wall surface 24 (the internal or external surface of the container 6', or the walls of the container 6' by themselves) is disposed opposite to and substantially parallel with the wall surface on which the light beams 1 and 3 with the wavelengths λ1 and λ2 are incident, and is adapted to reflect the light beams 1 and 3 with the wavelengths λ1 and λ2.

The light beams 1 and 3 with the wavelengths λ1 and λ2 emitted from the semiconductor light sources 2 and 4, respectively, are formed into substantially parallel beams at a tip portion 21 of the package 5' via which the beams emerge. The substantially parallel beams then pass through a lens 22' and are then shone on the container 6'. The beams 1 and 3 then enter the container 6' via an incident plane 23 thereof, pass through the sample solution 7, and then focused at and reflected by the reflecting plane 24 opposite to and substantially parallel with the incident plane of the container 6', producing reflected light beams 25. The reflected light beams 25 pass through the sample solution 7 again and exit the container 6' via the incident plane 23 thereof. The light beams 1 and 3 with the wavelengths λ1 and λ2 that have emerged out of the container 6' are formed into substantially parallel beams by the lens 22', and they are then focused onto the detector 9' after being formed by the tip portion 21 of the package 5' in the opposite manner to when they had emerged therefrom. The detector 9' is disposed between the semiconductor light sources 2 and 4, whose positions are adjusted such that the light beams 1 and 3 with the wavelengths λ1 and λ2 can be detected by the detector 9' efficiently.

The detector 9' is closely surrounded by a light-blocking wall 26 so as to prevent the light from the semiconductor light sources 2 and 4 from entering the detector 9', either directly from the light sources or in the form of stray light produced by the light from the semiconductor light source 2 or 4 having been reflected by the external wall of the package 5'. The light-blocking wall 26 is electrically conducting, so that it can prevent the electric signals from the oscillator circuit 10 and oscillator circuit 12 of Embodiment 1 shown in FIG. 1 from entering into semiconductor light sources 2 and 4 as noise.

In the present embodiment, the light beams 1 and 3 with the wavelengths λ1 and λ2 enter the container 6' via the incident plane 23, pass through the sample solution 7, and is then focused onto and reflected by the reflecting plane 24 disposed opposite to and substantially parallel with the incident plane of the container 6'. The reflected beams then pass through the sample solution 7 again and emerge out of the container 6' via the incident plane 23. Thus, the optical paths are twice as long, so that an increase in sensitivity can be achieved. In addition, because the light beams intersect with one another at the substantially ½ position of the length of the optical paths that are twice as long before they are reflected, the influence of concentration due to the difference in optical paths of the two beams of light can be eliminated, as in Embodiments 1 to 3. Furthermore, because the light sources and the detector are housed in the same package, the size of the apparatus can be reduced.

Embodiment 5

In Embodiments 1 to 4, the position at which the beams 1 and 3 with the wavelengths λ1 and λ2 intersect with one another is set to be the substantially ½ position of the length of the optical path, or the substantially ½ position of the length of the optical path that has been made twice as long by reflection. In the present embodiment, the intersecting position is different from those of the foregoing embodiments.

Figure 8:
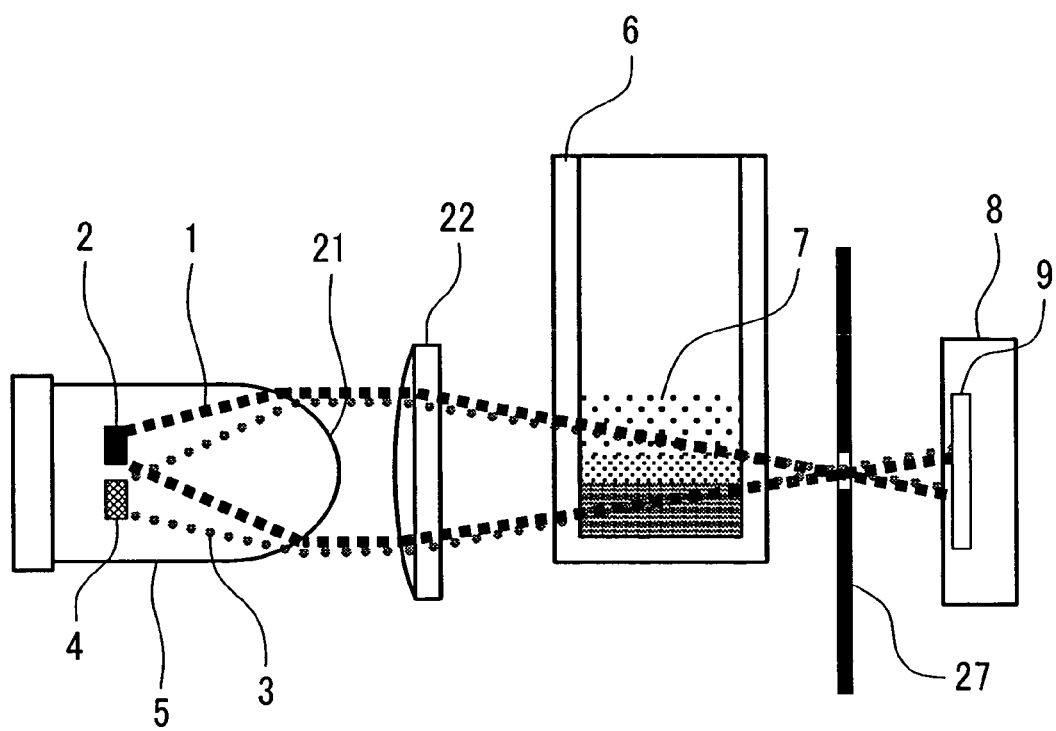
FIG. 8 shows another embodiment in which the point of intersection of the light beams with the wavelengths λ1 and λ2 is located between the container and the detector.

FIG. 8 schematically shows the present embodiment in which the aforementioned intersecting position is set to be located between the container 6 and detector 9. In this embodiment, the position of the semiconductor light sources 2 and 4 are adjusted such that the position at which the beams 1 and 3 with the wavelengths λ1 and λ2, respectively, is located between the container 6 and the detector 9. Because the intersecting position is located outside the container 6, an aperture 27 can be disposed at the intersecting position. The aperture 27 can be used to eliminate unwanted stray light other than the beams 1 (λ1) and 3 (λ2) that could be incident on the detector 9, thereby improving detection accuracy. It should be noted, however, that because the optical axis of the beam 1 with the wavelength λ1 and that of the beam 3 with the wavelength λ2 do not pass through the portion with the same concentration, the present embodiment cannot provide the advantage relating to the absence of influence of concentration due to the difference in the optical paths of the two beams, as described with reference to Embodiments 1 to 4. Thus, it is important to clarify the purpose before adopting the concept of the present embodiment.

Embodiment 6

Figure 9A:
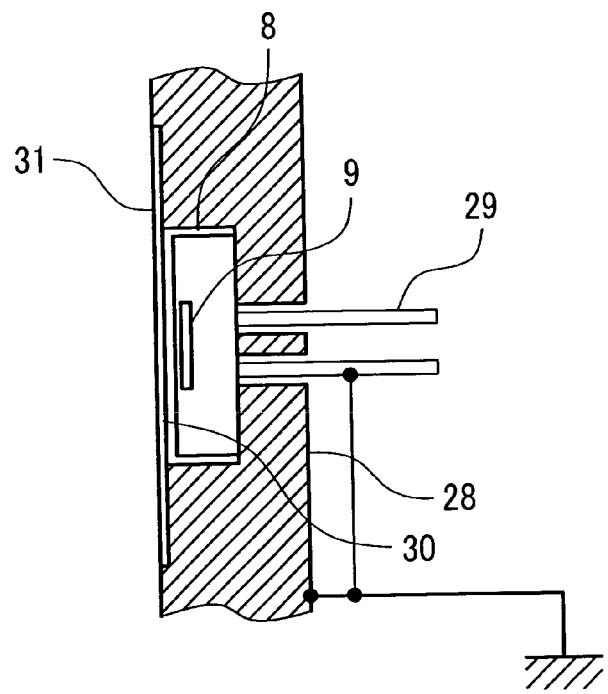
FIGS. 9A and 9B show methods of preventing noise in the various embodiments of the invention.
Figure 9B:
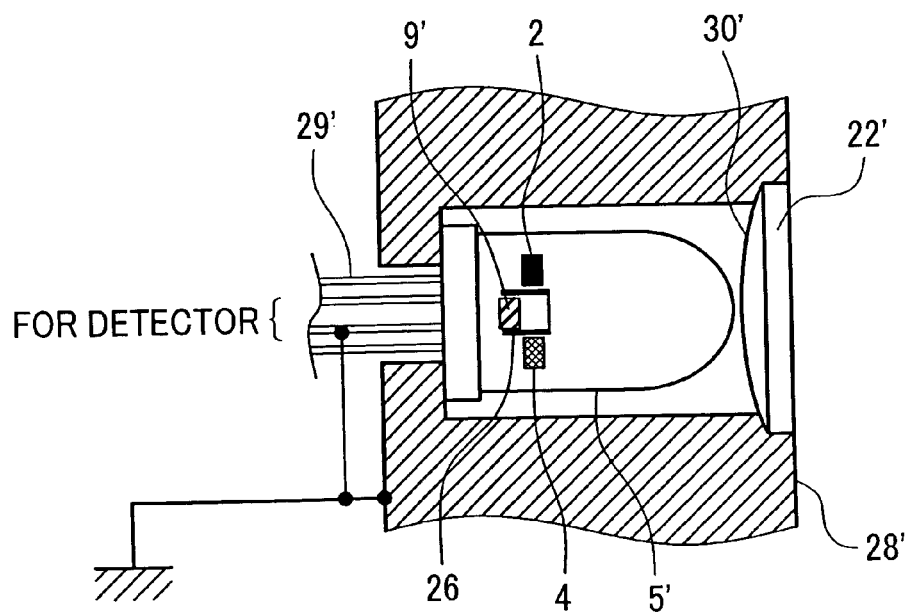

In Embodiments 1 to 3 and 5, as shown in FIG. 9(*a*), the detector 9 is housed in a conducting member 28 such that wiring leads 29 are not in contact with the conducting member. The incident plane of the detector 9 is covered with a transparent member 31 of thin glass or the like. The transparent member 31 is coated with a transparent electrically conducting film 30, such as an ITO, at least on that side thereof which is in contact with the conducting member 28. The conducting member 28 and the transparent film 30 are thus grounded so as to prevent noise. One of the two wiring leads 29 is grounded while the other is insulated from the surrounding members. Namely, the detection system is covered with planes that are almost all grounded except for one of the wiring leads, so that noise can be prevented.

Similarly, in Embodiment 4, package 5' containing the detector 9' and the semiconductor light sources 2 and 4 is contained in a conducting member 28' such that wiring leads 29' are not in contact with the conducting member 28', as shown in FIG. 9(*b*). The incident/outgoing plane of the package 5' is covered with a lens 22' coated with a transparent electrically conducting film 30', such as an ITO, at least on the side thereof that is in contact with the conducting member 28'. The conducting member 28', the transparent electrically conducting film 30', and the aforementioned light-blocking wall 26 are grounded so as to prevent noise. In FIG. 9(*b*), four wiring leads are shown as an example, of which two are used for detection. One of the detection leads is grounded while the other is insulated from the other surrounding members. Thus, the two light sources and most of the other portions except for one of the wiring leads are covered with planes that are grounded, so that noise can be prevented.

Similar effects may be obtained by covering the exterior of the detector 9 or the package 5' with a transparent electrically conducting film, such as an ITO, to the extent that the film is not in contact with the wiring leads 29 and 29', and connecting the film to ground.

Embodiment 7

In the present embodiment, the peak wavelength, or the wavelength for the greatest amount of a component, of the light emitted by the semiconductor light sources 2 and 4 is a particular combination of two different wavelengths selected from the group of 13 wavelengths consisting of substantially 340, 405, 415, 450, 480, 505, 546, 570, 600, 660, 700, 750, and 800 nm. By employing a combination of these wavelengths, the entire examination items that are currently measurable using automatic biochemical analyzers can be covered without changing the protocol of the reagents used. In the foregoing embodiments, of the possible combinations of the aforementioned frequencies, those including ultraviolet ray of the wavelength of 340 nm for one of the wavelengths are most likely. This is due to the fact that there are many examination items or examination reagents for which combinations of the wavelength of 340 nm and another wavelength are suitable. It is very important to select ultraviolet ray for one of the wavelengths of a combination.

The invention can be employed for analyzing components, such as biological components in particular.

What is claimed is:

1. A sample analyzer comprising:
a sample container for carrying a sample;
a first light source for emitting a first light beam of a first wavelength with which said sample is irradiated;
a second light source for emitting a second light beam of a second wavelength with which said sample is irradiated;
a package which houses said first light source and said second light source, the package refracting said first light beam from said first light source and said second light beam from said second light source so that said first light beam and said second light beam extend in substantially a same direction and intersect each other in said sample;
a detector for detecting a first beam of light which is said first light beam of said first wavelength that has passed through said sample, and a second beam of light which is said second light beam of said second wavelength that has passed though said sample;
wherein said first light beam of said first wavelength intersects with said second light beam of said second wavelength at a substantially ½ position in said sample of the length of said beams in the direction of transmission thereof.

2. The sample analyzer according to claim 1, wherein said first light source and said second light source comprise semiconductor lasers.

3. The sample analyzer according to claim 1, further comprising:
a first oscillator circuit for modulating said light beam of said first wavelength into a first frequency;
a second oscillator circuit for modulating said light beam of said second wavelength into a second frequency; and
a frequency separation circuit for separating a signal detected by said detector into components of said first frequency and said second frequency.

4. The sample analyzer according to claim 1, wherein said detector comprises a photodiode with a photo-receiving plane thereof being covered with a transparent electrically conducting film that is grounded, said photodiode having two electrodes of which one is grounded, said photodiode being almost entirely covered with planes connected to ground except for the other of said two electrodes thereof.

5. The sample analyzer according to claim 1, wherein the wavelength of one of the light beams emitted by said first light source and said second light source is that of an ultraviolet ray.

6. The sample analyzer according to claim 1, wherein the peak wavelengths of the light beams emitted by said first light source and said second light source, or the wavelengths of said light beams at which the maximum amounts of components are obtained, are two different wavelengths selected from the group consisting of substantially 340, 405, 415, 450, 480, 505, 546, 570, 600, 660, 700, 750, and 800 (nm).

7. A sample analyzer comprising:
a sample container for carrying a sample;
a first light source for emitting a first light beam of a first wavelength with which said sample is irradiated;
a second light source for emitting a second light beam of a second wavelength with which said sample is irradiated;
a package which houses said first light source and said second light source, the package refracting said first light beam from said first light source and said second light beam from said second light source so that said first light beam and said second light beam extend in substantially a same direction and intersect each other in said sample;
a detector for detecting a first light beam which is said light beam of said first wavelength that has passed through said sample, and a second light beam which is said light beam of said second wavelength that has passed through said sample, wherein
the relationship $P<a/b(W-D)$ is satisfied, where a is the distance between said first and second light sources and X, which is a position in the horizontal direction at which said light beams of said first and second wavelengths intersect with one another; b is the distance between X and said detector; P is the distance between said first and said second light sources; W is the width of a photo-receiving plane of said detector; D is the maximum diameter on said photo-receiving plane of said first and said second light beams emitted by said first and said second light sources, respectively; and Q is the distance between the centers of said first and said second light beams on said photo-receiving plane, wherein X is located at a substantially ½ position in said sample of the length of said beams in the direction of transmission thereof in the horizontal direction.

8. The sample analyzer according to claim 7, wherein said first and said second light sources are housed in a single package.

9. A sample analyzer comprising:
a sample container for carrying a sample;
a first light source for emitting a first light beam of a first wavelength with which said sample is irradiated;
a second light source for emitting a second light beam of a second wavelength with which said sample is irradiated;
a package which houses said first light source and said second light source, the package refracting said first light beam from said first light source and said second light beam from said second light source so that said first light beam and said second light beam extend in substantially a same direction and intersect each other in said sample:
a detector for detecting a first light beam which is said first light beam of said first wavelength that has passed through said sample, and a second light beam which is said second light beam of said second wavelength that has passed through said sample, wherein
said sample container comprises a transparent portion and a reflecting portion that reflects light, wherein said sample is irradiated with said first light beam of said first wavelength and said second light beam of said second wavelength via said transparent portion of said sample container, said light beams passing through said sample and then being reflected by said reflecting portion, said light beams again passing through said sample and emerging via said transparent portion to be detected by said detector, and wherein
said first light source, said second light source, and said detector are disposed such that said first light beam of said first wavelength and said second light beam of said second wavelength can be captured by said detector after intersecting with one another substantially at said reflecting portion and reflected thereby.

10. The sample analyzer according to claim 9, wherein said detector is disposed between said first light source and said second light source.

11. The sample analyzer according to claim 9, wherein a light-blocking wall is provided around said detector.

12. The sample analyzer according to claim 9, wherein said detector comprises a photodiode of which at least a photo-receiving plane is covered with a transparent, electrically conducting film that is grounded, said photodiode having two electrodes of which one is grounded, and wherein almost all of the parts are entirely covered with planes that are connected to ground except for the other of said two electrodes and the electrodes of said first light source and said second light source.

* * * * *